US00PP30766P3

(12) United States Plant Patent
Uchneat

(10) Patent No.: US PP30,766 P3
(45) Date of Patent: Jul. 30, 2019

(54) ***LAGERSTROEMIA* PLANT NAMED 'G2X13368'**

(50) Latin Name: *Lagerstroemia indica*
Varietal Denomination: G2X13368

(71) Applicant: Michael S Uchneat, Bellefonte, PA (US)

(72) Inventor: Michael S Uchneat, Bellefonte, PA (US)

(73) Assignee: Garden Genetics LLC, Bellefonte, PA (US)

( * ) Notice: Subject to any disclaimer, the term of this patent is extended or adjusted under 35 U.S.C. 154(b) by 0 days.

(21) Appl. No.: 15/732,450

(22) Filed: Nov. 15, 2017

(65) Prior Publication Data

US 2019/0150346 P1 May 16, 2019

(51) Int. Cl.
*A01H 5/02* (2018.01)
*A01H 6/00* (2018.01)

(52) U.S. Cl.
USPC ..... Plt./252
CPC ..... *A01H 6/00* (2018.05); *A01H 5/02* (2013.01)

(58) Field of Classification Search
USPC ..... Plt./226, 252
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct *Lagerstroemia* cultivar named 'G2X13368' is disclosed, characterized by vibrant purple flowers. Plants are highly floriferous and compact. The new variety is a *Lagerstroemia*, normally used for outdoor ornamental purposes.

2 Drawing Sheets

Figure 1:
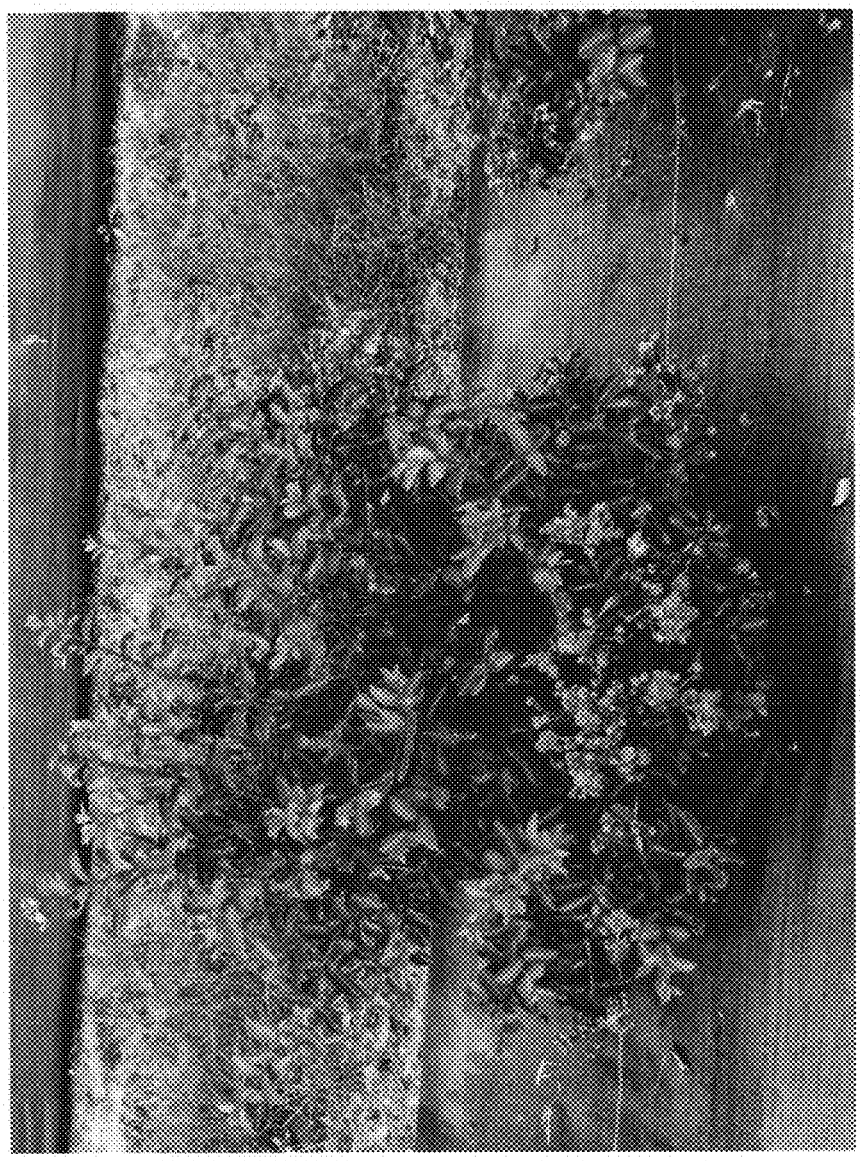

Latin name of the genus and species: *Lagerstroemia indica.*

Variety denomination: 'G2X13368'.

BACKGROUND OF THE INVENTION

The new *Lagerstroemia* cultivar is a product of a planned breeding program conducted by the inventor, Michael Uchneat, in Bellefonte, Pa. The objective of the breeding program was to develop a compact *Lagerstroemia* exhibiting the characteristics of winter hardiness consistently superior to present compact and traditional market genotypes; heat tolerance equal to market genotypes; a fully mounded habit with superior branching and floral coverage; reblooming; multiple colors in a well-matched collection; dark green foliage; powdery mildew resistance; and excellent propagation characteristics from vegetative cutting. The cross pollination resulting in this new variety was made during August of 2010.

The seed parent is the unpatented commercial variety referred to as *Lagerstroemia* '3876-1'. The pollen parent is *Lagerstroemia* 'Violet Filli' U.S. Plant Pat. No. 14,267. The new variety was selected September of 2011 by the inventor in a group of seedlings resulting from the 2010 crossing, in a seedling trial field in Bellefonte, Pa.

Asexual reproduction of the new cultivar was performed by softwood cuttings. This was first performed at Spring Meadow Nursery in Bellefonte, Pa. during February of 2012 and has shown that the unique features of this cultivar are stable and reproduced true to type in multiple successive generations.

SUMMARY OF THE INVENTION

The cultivar 'G2X13368' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'G2X13368' These characteristics in combination distinguish 'G2X13368' as a new and distinct *Lagerstroemia* cultivar:

1. Vibrant purple flowers.
2. Compact plants.
3. Very floriferous plants.

Plants of the new cultivar 'G2X13368' are similar to plants of the seed parent, *Lagerstroemia* '3876-1' in most horticultural characteristics; however, plants of the new cultivar 'G2X13368' differ in the following;

1. The new variety has a purple colored flower, the seed parent has flowers in shades of pink.
2. The new variety has good basal branching, the seed parent has loose branching.
3. The new variety has good cold tolerance, the seed parent has not as much tolerance for cold.

Plants of the new cultivar 'G2X13368' are similar to plants of the pollen parent, *Lagerstroemia* 'Violet Filli' in most horticultural characteristics; however, plants of the new cultivar 'G2X13368' differ in the following;

1. The new variety has good basal branching, the pollen parent has loose branching.
2. The new variety has good cold tolerance, the pollen parent has not as much tolerance.

COMMERCIAL COMPARISON

Plants of the new cultivar 'G2X13368' are comparable to the commercial variety *Lagerstroemia* 'G2X133251', U.S. Plant Pat. No. 27,633. The two *Lagerstroemia* varieties are similar in most horticultural characteristics; however, the new variety 'G2X13368' differs in the following;

1. The new variety has darker, vibrant purple flowers, comparator has lighter purple flowers.
2. New variety branches grow upwards and outwards, comparator's branches arch over.

BRIEF DESCRIPTION OF THE PHOTOGRAPHS

The accompanying photograph in FIG. 1 illustrates in full color a typical plant of 'G2X13368' in a 3 gallon pot. Age of the plant photographed is approximately 2 years old from a rooted cutting.

Figure 2:
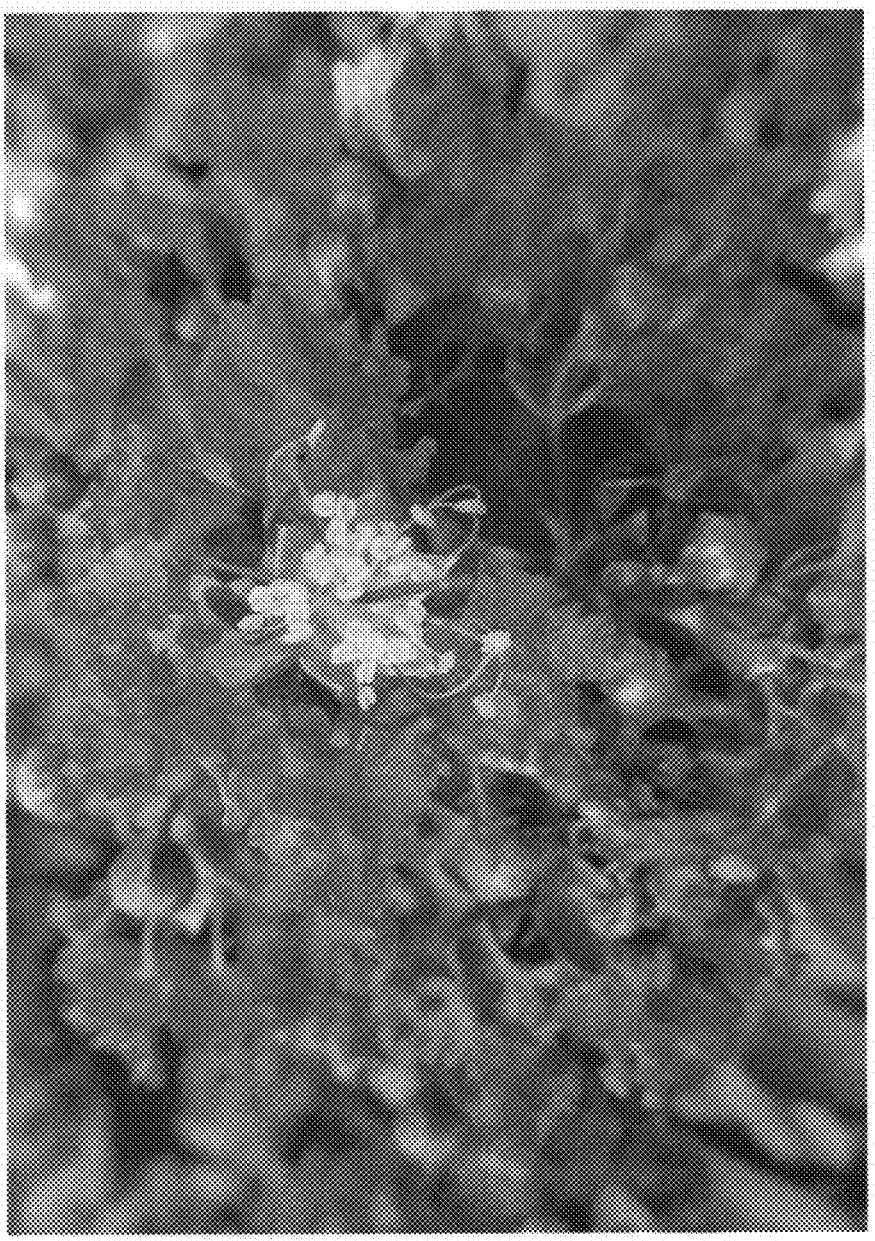

FIG. 2 illustrates a close up view of the inflorescence.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'G2X13368' plants grown in a poly house during July of 2017 Grand Haven. Mich. The growing temperature ranged from approximately 18° C. to 27° C. during the day and from approximately 5° C. to 10° C. during the night. General light conditions are normal sunlight and numerical values represent averages of typical plant types.

Botanical classification: *Lagerstroemia indica* 'G2X13368'.

PROPAGATION

Type of propagation typically used: Terminal vegetative cutting.

Time to initiate roots: About 14-21 days at about 24° C.

Time to produce a rooted cutting: About 28-35 days at about 24° C.

Root description: Thin fibrous, not fleshy, freely branching. White in color, not accurately measured with R.H.S. Chart.

PLANT

Age of plant described: 2-3 years old from a rooted cutting.
Container size: 3 gallon container.
Overall plant shape: Upright.
Growth habit: Freely branching upward and outward.
Plant spread: 81 cm.
Plant height: 71 cm.
Growth rate: Good.
Plant vigor: Good.
Branching habit: Basal, freely branching.
Length of primary lateral branches: 38 cm.
Diameter of lateral branches: 4 mm.
Quantity of lateral branches: 7.
Stem:
- *Color*.—Edges — Brown 200A blending to Red 47C in new growth. Sides — Brown 200A blending to Greyed-green 193A in new growth.
- *Shape*.—Square.
- *Strength*.—Strong.
- *Aspect angle*.—5-95°.
- *Texture*.—Pubescent with young, then woody with age.

Internode length: 0.5 to 1.5 cm.

FOLIAGE

Leaf:
- *Arrangement*.—Sub-opposite to alternate.
- *Average length*.—2-4 cm.
- *Average width*.—1.25 to 2.5 cm.
- *Shape of blade*.—Elliptical.
- *Apex*.—Acute.
- *Base*.—Oblique.
- *Margin*.—Entire.
- *Texture of top surface*.—Smooth.
- *Texture of bottom surface*.—Smooth, waxy, can feel veins.
- *Color*.—Young foliage upper side: Green 143A. Young foliage under side: Green 143C. Mature foliage upper side: Green 143A. Mature foliage under side: Green 143C.
- *Venation*.—Type: Pinnate. Venation color upper side: Greyed-Yellow 161C. Venation color under side: Yellow-Green 145C.
- *Petiole*.—Length: 1 mm. Diameter: 1 mm. Texture, upper side: Smooth. Texture, under side: Smooth. Color, upper side: Greyed-Yellow 161C. Color, under side: Yellow-Green 145C.

FLOWER

Natural flowering season: Late Summer.
Inflorescence form: Panicles.
Flowers per inflorescence: Average 9, with 30 to 60 unopened buds.
Inflorescence size:
- *Width*.—12 cm.
- *Height*.—10 cm.

Individual flowers:
- *Type*.—Rotate.
- *Shape*.—Obovate.
- *Habit*.—Whorled outward.
- *Diameter*.—4 cm.
- *Length*.—4 cm.
- *Depth*.—2 cm.
- *Persistence*.—Self-cleaning.
- *Fragrance*.—None.

Petals:
- *Arrangement*.—Whorled.
- *Number*.—6.
- *Shape*.—Loosely edged and undulate orbit shape.
- *Margin*.—Loose, undulate.
- *Tip shape*.—Rounded.
- *Base shape*.—Rounded.
- *Length*.—Average 1.1 cm.
- *Width*.—Average 1.3 cm.
- *Texture*.—Upper: Soft, smooth, delicate. Lower: Soft, smooth, delicate.
- *Color*.—When opening: Upper surface: Purple-violet N80A. Under surface: Purple-violet N80A. Fully opened: Upper surface: Purple-violet N80A. Under surface: Purple-violet N80A. Fading: Upper surface: Purple-violet N80A. Under surface: Purple-violet N80A.

Bud:
*Shape*.—Obovate.
*Length*.—7 mm.
*Diameter*.—9 mm.
*Color*.—Greyed-red 182A.
Sepals:
*Appearance*.—Triangular.
*Arrangement*.—Unguiculate.
*Shape*.—Narrowly triangular.
*Tip shape*.—Acute.
*Base shape*.—Obtuse.
*Margin*.—Entire.
*Quantity per flower*.—6.
*Length*.—5 mm.
*Width*.—4 mm.
*Margin*.—Entire.
*Texture*.—Upper: Smooth, coriaceous, rugose. Lower: Smooth.
*Color*.—Upper: Yellow-Green Group 145C blended with Red-Purple Group 60A. Lower: Yellow-Green 145C.
Calyx:
*Shape*.—Unguiculate.
*Length*.—5 mm.
*Diameter*.—5 mm.
Peduncle:
*Length*.—1 cm.
*Diameter*.—0.5-1 mm.
*Texture*.—Smooth.
*Color*.—Yellow-Green Group 145B blended with Red-Purple Group 60A.
*Orientation*.—Upright and outward.
*Strength*.—Good.
Pedicel:
*Length*.—9 mm.
*Diameter*.—0.5-1 mm.
*Angle*.—5-35 degrees.
*Strength*.—Good.
*Texture*.—Smooth.
*Color*.—Yellow-Green Group 145B blended with Red-Purple Group 60A.

REPRODUCTIVE ORGANS

Stamens:
*Number*.—About 30.
*Filament length*.—0.8-1.8 cm.
*Filament color*.—Red-Purple Group 63A.
Anthers:
*Shape*.—Orbital.
*Length*.—1 mm.
*Color*.—Yellow-Orange Group 15B.
*Pollen*.—Amount: Good. Color: Yellow 12B.
Pistil:
*Number*.—1.
*Length*.—1.85 mm.
*Style*.—Length: 1.9 cm. Color: Red Group 53B.
Stigma:
*Shape*.—Globe.
*Color*.—Yellow-Green Group 152B.
*Ovary color*.—Yellow Group 11B.

OTHER CHARACTERISTICS

Fruits and seeds: Not observed to date.
Disease/pest resistance: Neither resistance nor susceptibility to normal diseases and pests of *Lagerstroemia* observed.
Temperature range: Observed to tolerate a temperature range from −28° C. to 35° C. Root hardy to −28C, top of the plant does die back to the ground.

What is claimed is:

1. A new and distinct cultivar of *Lagerstroemia* plant named 'G2X13368' as herein illustrated and described.

* * * * *